United States Patent
Pitzele et al.

(10) Patent No.: US 6,545,170 B2
(45) Date of Patent: Apr. 8, 2003

(54) 2-AMINO-5, 6 HEPTENOIC ACID DERIVATIVES USEFUL AS NITRIC OXIDE SYNTHASE INHIBITORS

(75) Inventors: Barnett S. Pitzele, Skokie, IL (US); James A. Sikorski, Kirkwood, MO (US); Donald W. Hansen, Jr., Skokie, IL (US); Ronald Keith Webber, St. Charles, MO (US); Mihaly V. Toth, St. Louis, MO (US); Jeffrey A. Scholten, Chesterfield, MO (US); Jeffrey S. Snyder, Manchester, MO (US)

(73) Assignee: Pharmacia Corporation, Chicago, IL (US)

( * ) Notice: Subject to any disclaimer, the term of this patent is extended or adjusted under 35 U.S.C. 154(b) by 0 days.

(21) Appl. No.: 09/835,185

(22) Filed: Apr. 13, 2001

(65) Prior Publication Data

US 2002/0143061 A1 Oct. 3, 2002

Related U.S. Application Data

(60) Provisional application No. 60/196,794, filed on Apr. 13, 2000.

(51) Int. Cl.[7] .............................................. C07C 101/00
(52) U.S. Cl. ...................... 554/104; 514/558; 514/560; 514/561; 562/439
(58) Field of Search .................... 554/104; 562/439; 514/558, 560, 561

(56) References Cited

U.S. PATENT DOCUMENTS

| | | | |
|---|---|---|---|
| 5,132,453 A | 7/1992 | Griffith | 562/560 |
| 5,684,008 A | 11/1997 | Hallinan et al. | 514/256 |
| 5,830,917 A | 11/1998 | Moore et al. | 514/634 |
| 5,854,251 A | 12/1998 | Hallinan et al. | 514/256 |
| 5,863,931 A | 1/1999 | Beams et al. | 514/357 |
| 5,919,787 A | 7/1999 | Hallinan et al. | 514/256 |
| 5,945,408 A | 8/1999 | Webber et al. | 514/63 |
| 5,981,511 A | 11/1999 | Gapud et al. | 514/63 |
| 5,994,391 A | 11/1999 | Lee et al. | 514/431 |
| 6,169,089 B1 | 1/2001 | Hallinan et al. | 514/256 |

FOREIGN PATENT DOCUMENTS

| | | | |
|---|---|---|---|
| EP | 04 46699 | 5/2000 | C07K/5/06 |
| EP | 05 21471 | 10/2000 | C07D/239/42 |
| WO | WO 93 13055 | 7/1993 | C07C/257/14 |
| WO | WO 93 16055 | 8/1993 | C07D/281/10 |
| WO | WO 94 12165 | 6/1994 | A61K/31/155 |
| WO | WO 94 14780 | 7/1994 | C07D/239/48 |
| WO | WO 95 11014 | 4/1995 | A61K/31/00 |
| WO | WO 95 11231 | 4/1995 | C07D/207/22 |
| WO | WO 95 25382 | 9/1995 | H03H/17/02 |
| WO | WO 95 25717 | 9/1995 | C07C/257/14 |
| WO | WO 96 15120 | 5/1996 | C07D/257/06 |
| WO | WO 96 33175 | 10/1996 | C07D/223/12 |
| WO | WO 96 35677 | 11/1996 | C07D/223/12 |
| WO | WO 97 06802 | 2/1997 | A61K/31/495 |
| WO | WO 99 29865 | 6/1999 | C12N/15/28 |
| WO | WO 99 46240 | 9/1999 | C07N/257/14 |

OTHER PUBLICATIONS

S. Moncafa and E. Higgs, *Molecular Mechanisms and Therapeutic Strategies Related to Nitric Oxide* 1995, FASEB J., 9, 1319–1330.

S. Rozen, I. Shahak, and E. Bergmann, *Organic Fluorine Compounds Part XLIV. Preparation and Reactions of Epifluorohydrin* 1971, Synthesis 646–7.

E. Bergmann, S. Cohen, and I. Shahak, *Organic Fluorine Compounds. Part XX. Some Reactions of 1–Chloro–3–fluoropropan–2–ol and Epifluorohydrin* 1961, J Chem Soc 3448–52.

A. Jeanguenat and D. Seebach, *Stereoselective Chain Elongation at C–3 of Cysteine through 2,3–Dihydrothiazoles, Without Racemization, Preparation of 2–Amino–5–hydroxy–3–mercapto alkanoic Acid Derivatives.* 1991, J. Chem. Soc. Perkin Trans. I, 2291–8.

G. Pattenden, S. Thom, and M. Jones, *Enantioselective Synthesis of 2–Alkyl Substituted Cysteines.* 1993, Tetrahedron, 49, 2131.

D. Bredt and S. Synder, *Isolation of nitric oxide syhthetase, a calmodulin–requiring enzyme.* 1990 Proc. Natl. Acad. Sci. U.S.A., 87, 682–685.

Moore et al, *2–Iminopiperidine and Other 2–Iminoazheterocycles as Potent Inhibitors of Human Nitric Oxide Synthase Isoforms* 1996 J. Med. Chem., 39, 669–672.

T. Misko et al, *A Fluorometric Assay for the Measurement of Nitrite in Biological Samples* 1993, Analytical Biochemistry, 214, 11–16.

Y. Lee et al., *Conformationally–restricted Arginine Analogues as Alternative Substrates and Inhibitors of Nitric Oxide Synthases* 1999 Bioorg. Med. Chem. 7 1097–1104.

R. Young et al.., *Inhibition of Inducible Nitric Oxide Synthase by Acetamidine Derivatives of Hetero–Substituted Lysine and Homolysine* 2000 Bioorg. Med. Chem. Lett. 10 597–600.

*Primary Examiner*—Deborah D. Carr
(74) *Attorney, Agent, or Firm*—Philip B. Polster, II

(57) ABSTRACT

The present invention contains novel compounds useful as nitric oxide synthase inhibitors.

30 Claims, No Drawings

2-AMINO-5, 6 HEPTENOIC ACID DERIVATIVES USEFUL AS NITRIC OXIDE SYNTHASE INHIBITORS

CROSS REFERENCE TO RELATED APPLICATIONS

This application claims the benefit of U.S. Provisional Application Serial No.60/196,794, filed Apr. 13, 2000.

BACKGROUND OF THE INVENTION

1. Field of the Invention

The present invention relates to novel compounds and their use in therapy, in particular their use as nitric oxide synthase inhibitors.

2. Related Art

It has been known since the early 1980's that the vascular relaxation caused by acetylcholine is dependent on the presence of the vascular endothelium and this activity was ascribed to a labile humoral factor termed endothelium-derived relaxing factor (EDRF). The activity of nitric oxide (NO) as a vasodilator has been known for well over 100 years. In addition, NO is the active component of amylnitrite, glyceryltrinitrate and other nitrovasodilators. The identification of EDRF as NO has coincided with the discovery of a biochemical pathway by which NO is synthesized from the amino acid L-arginine by the enzyme NO synthase.

Nitric oxide is the endogenous stimulator of the soluble guanylate cyclase. In addition to endothelium-dependent relaxation, NO is involved in a number of biological actions including cytotoxicity of phagocytic cells and cell-to-cell communication in the central nervous system.

There are at least three types of NO synthase as follows:

(i) a constitutive, Ca++/calmodulin dependent enzyme, located in the endothelium, that releases NO in response to receptor or physical stimulation.

(ii) a constitutive, Ca++/calmodulin dependent enzyme, located primarily in the brain, that releases NO in response to receptor or physical stimulation.

(iii) a Ca++ independent enzyme which is induced after activation of vascular smooth muscle,macrophages, endothelial cells, and a number of other cells by endotoxin and cytokines. Once expressed this inducible NO synthase generates NO continuously for long periods.

The NO released by the two constitutive enzymes acts as a transduction mechanism underlying several physiological responses. The NO produced by the inducible enzyme is a cytotoxic molecule for tumor cells and invading microorganisms. It also appears that the adverse effects of excess NO production, in particular pathological vasodilation and tissue damage, may 10 result largely from the effects of NO synthesized by the inducible NO synthase.

There is a growing body of evidence that NO may be involved in the degeneration of cartilage which takes place in certain conditions such as arthritis and it is also known that NO synthesis is increased in rheumatoid arthritis and in osteoarthritis. Accordingly, conditions in which there is an advantage in inhibiting NO production from L-arginine include arthritic conditions such as rheumatoid arthritis, osteoarthritis, gouty arthritis, juvenile arthritis, septic arthritis, spondyloarthritis, acute rheumatic arthritis, enteropathic arthritis, neuropathic arthritis, and pyogenic arthritis.

Other conditions which NO inhibition may be useful include chronic or inflammatory bowel disease, cardivascular ischemia, diabetes, congestive heart failure, myocarditis, atherosclerosis, migraine, glaucoma, aortic aneurysm, reflux esophagitis, diarrhea, irritable bowel syndrome, cystic fibrosis, emphysema, asthma, bronchiectasis, hyperalgesia (allodynia), cerebral ischemia (both focal ischemia, thrombotic stroke and global ischemia (secondary to cardiac arrest), multiple sclerosis and other central nervous system disorders mediated by NO, for example Parkinson's disease and Alzheimer's disease. Further neurodegenerative disorders in which NO inhibition may be useful include nerve degeneration and/or nerve necrosis in disorders such as hypoxia, hypoglycemia, epilepsy, and in external wounds (such as spinal cord and head injury), hyperbaric oxygen convulsions and toxicity, dementia e.g. pre-senile dementia, and AIDS-related dementia, Sydenham's chorea, Huntington's disease, Amyotrophic Lateral Sclerosis, Korsakoff's disease, imbecility relating to a cerebral vessel disorder, sleeping disorders, schizophrenia, depression, depression or other symptoms associated with Premenstrual Syndrome (PMS), anxiety and septic shock.

Nitric oxide inhibition may also play a role in the treatment of pain including somatogenic (either nociceptive or neuropathic), both acute and chronic. A nitric oxide inhibitor could be used in any situation that a common NSAID or opioid analgesic would traditionally be administered.

Still, other disorders which may be treated by inhibiting NO production include opiate tolerance in patients needing protracted opiate analgesics, and benzodiazepine tolerance in patients taking benzodiazepines, and other addictive behavior, for example, nicotine and eating disorders. NO inhibiting agents may also be useful as antibacterial agents.

Further conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy.

Other conditions in which there is an advantage in inhibiting NO production include ocular conditions such as ocular hypertension retinitis uveitis, systemic lupus erythematosis (SLE), flomerulonephritis, restenosis, inflammatory sequelae of viral infections, acute respiratory distress syndrome (ARDS), oxidant-induced lung injury, IL2 therapy such as in a cancer patient, cachexia, immunosuppression such as in transplant therapy, disorders of gastrointestinal motility, sunburn, eczema, psoriasis, and bronchitis.

Some of the NO synthase inhibitors proposed for therapeutic use are non-selective; they inhibit both the constitutive and the inducible NO synthases. Use of such a non-selective NO synthase inhibitor requires that great care be taken in order to avoid the potentially serious consequences of over-inhibition of the constitutive NO-synthase including hypertension and possible thrombosis and tissue damage. In particular, in the case of the therapeutic use of L-NMMA for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use (S. Moncada and E. Higgs, FASEB J., 9, 1319–1330, 1995).

The following individual publications disclose compounds said to be useful in nitric oxide synthase inhibition:

International Publication No. WO 96/35677

International Publication No. WO 96/33175

International Publication No. WO 96/15120
International Publication No. WO 95/11014
International Publication No. WO 95/11231
International Publication No. WO 95/25717
International Publication No. WO 95/24382
International Publication No. WO 94/12165
International Publication No. WO 94/14780
International Publication No. WO 93/13055
European Patent Application No. EP0446699A1
U.S. Pat. No. 5,132,453
U.S. Pat. No. 5,684,008
U.S. Pat. No. 5,830,917
U.S. Pat. No. 5,854,251
U.S. Pat. No. 5,863,931
U.S. Pat. No. 5,919,787
U.S. Pat. No. 5,945,408
U.S. Pat. No. 5,981,511

The disclosures of which are hereby incorporated by reference in their entirety as if written herein.

In particular, WO 93/13055 discloses compounds of the formula

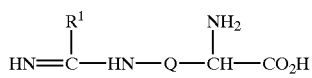

and salts, and pharmaceutically acceptable esters and amides thereof, in which:

$R^1$ is a $C_{1-6}$ straight or branched chain alkyl group, a $C_{2-6}$ alkenyl group, a $C_3$–$C_6$ cycloalkyl group or a $C_{3-6}$cycloalkyl$C_{1-6}$alkyl group;

Q is an alkylene, alkenylene or alkynylene group having 3 to 6 carbon atoms and which may optionally be substituted by one or more $C_{1-3}$ alkyl groups; a group of formula—$(CH_2)_pX(CH_2)_q$— where p is 2 or 3, q is 1 or 2 and X is $S(O)_x$ where x is 0, 1 or 2, O or $NR^2$ where $R^2$ is H or $C_{1-6}$alkyl; or a group of formula —$(CH_2)_rA(CH_2)_s$— where r is 0, 1 or 2, s is 0, 1 or 2 and A is a 3 to 6 membered carbocyclic or heterocyclic ring which may optionally be substituted by one or more suitable substituents such as $C_{1-6}$alkyl, $C_{1-6}$alkoxy, hydroxy, halo, nitro, cyano, trifluoro$C_{1-6}$alkyl, $C_{1-6}$alkoxy, hydroxy, halo, nitro, cyano, trifluoro$C_{1-6}$alkyl, amino, $C_{1-6}$alkylamino or di$C_{1-6}$alkylamino.

Various attempts have been made to improve the potency and selectivity of Nitric Oxide Synthase (NOS) inhibitors by adding one or more rigidifying elements to the inhibitor's structure. Publications by Y. Lee et al (*Bioorg. Med. Chem.* 7, 1097 (1999)) and R. J. Young et al (*Bioorg. Med. Chem. Lett.* 10, 597 (2000)) teach that imposing conformational rigidity with one or more carbon-carbon double bonds is not a favorable approach to impart selectivity for NOS inhibitors. In particular, the publication by Y. Lee et al (*Bioorg. Med. Chem.* 7, 1097 (1999)) teaches that when a carbon-carbon double bond is used to constrain the arginine backbone, the geometric isomer placing the carbon framework in a cis or Z orientation produces a less favorable interaction with NOS. In contrast, olefinic derivatives of arginine placing the carbon framework in the trans or E configuration are better substrates.

SUMMARY OF THE INVENTION

Compounds have now been found which have the advantage of being very efficacious in the human cartilage explant assay, a model for osteoarthritis.

The present invention demonstrates that a carbon-carbon double bond can be used as a rigidifying element, and the resulting compounds have unexpected potency and selectivity for inhibition of inducible NOS. The present invention also demonstrates that a carbon-carbon double bond imparts a highly favorable interaction with inducible NOS, such that the resulting compounds have unexpected potency and selectivity for inhibition of inducible NOS over the constitutive isoforms.

In a broad aspect, the present invention is directed to novel compounds, pharmaceutical compositions and methods of using said compounds and compositions for inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase. It is also another object of the present invention to lower nitric oxide levels in a subject in need of such lowering. The present compounds possess useful nitric oxide synthase inhibiting activity, and are expected to be useful in the treatment or prophylaxis of a disease or condition in which the synthesis or over synthesis of nitric oxide forms a contributory part.

In one embodiment of the present invention, the compounds are represented by Formula I, II or III

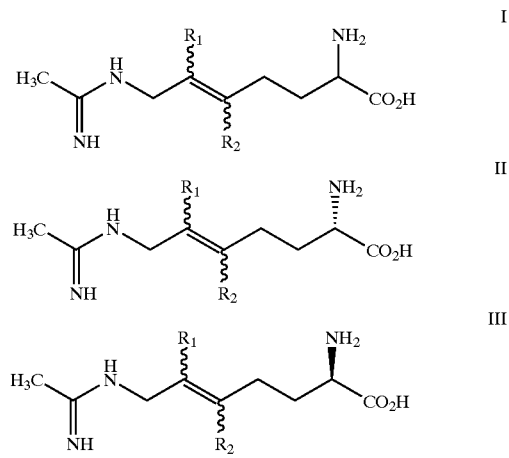

or a pharmaceutically acceptable salt thereof, wherein:

$R_1$ is H or methyl;

$R_2$ is H or methyl.

In another embodiment of Formula I, II or III, the compounds are represented wherein:

$R_1$ is H; and $R_2$ is H or methyl.

In another embodiment of Formula I, II or III, the compounds are represented wherein:

$R_1$ is H; and $R_2$ is methyl.

In another embodiment the compounds are represented by Formula I, II or III wherein:

$R_1$ is H; and $R_2$ is H.

Formula I, II or III may also be represented wherein:

$R_1$ is methyl; and $R_2$ is H or methyl.

Another embodiment of the invention is Formula I, II or III wherein:

$R_1$ is methyl; and $R_2$ is H.

The compounds of Formula I, II or III may also be represented wherein:

$R_1$ is methyl; and $R_2$ is methyl.

The compounds may also be represented wherein:

$R_1$ is H or methyl; and $R_2$ is H.

DETAILED DESCRIPTION OF THE INVENTION

The present invention provides compounds having a carbon-carbon double bond, and these compounds have unexpected greater potency and selectivity for inhibition of inducible NOS.

Compounds of the present invention are unexpectedly potent and highly selective inhibitors of inducible nitric oxide synthase, and exhibit a relatively long half life in vivo as compared with known nitric oxide synthase inhibitors.

Compounds of Formulas I, II, III, IV, V and VI will be useful for treating, among other things, inflammation in a subject, or for treating other nitric oxide synthase-mediated disorders, such as, as an analgesic in the treatment of pain and headaches. The compounds of the present invention will be useful in the treatment of pain including somatogenic (either nociceptive or neuropathic), both acute and chronic, and could be used in a situation including neuropathic pain for which a common NSAID or opioid analgesic would traditionally be administered.

Conditions in which the compounds of the present invention will provide an advantage in inhibiting NO production from L-arginine include arthritic conditions. For example, compounds of the present invention will be useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis.

Compounds of the invention will be further useful in the treatment of asthma, bronchitis, menstrual cramps (e.g., dysmenorrhea), premature labor, tendinitis, bursitis, skin-related conditions such as psoriasis, eczema, burns, sunburn, dermatitis, pancreatitis, hepatitis, and post-operative inflammation including inflammation from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis.

Compounds of the invention would be useful in treating inflammation and tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as glaucoma, retinitis, retinopathies, uveitis, ocular photophobia, and of inflammation and pain associated with acute injury to the eye tissue. Of particular interest among the uses of the present inventive compounds is the treatment of glaucoma, especially where symptoms of glaucoma are caused by the production of nitric oxide, such as in nitric oxide-mediated nerve damage. The compounds would also be useful in the treatment of pulmonary inflammation, such as that associated with viral infections and cystic fibrosis. The compounds would also be useful for the treatment of certain central nervous system disorders, such as cortical dementias including Alzheimer's disease, and central nervous system damage resulting from stroke, ischemia and trauma. These compounds would also be useful in the treatment of allergic rhinitis, respiratory distress syndrome, endotoxin shock syndrome, and atherosclerosis. The compounds would also be useful in the treatment of pain, including but not limited to postoperative pain, dental pain, muscular pain, pain caused by temporalmandibular joint syndrome, and pain resulting from cancer. The compounds would be useful for the prevention of dementias, such as Alzheimer's disease.

Besides being useful for human treatment, these compounds are also useful for veterinary treatment of companion animals, exotic animals and farm animals, including mammals and other vertebrates. More preferred animals include horses, dogs, and cats.

The present compounds may also be used in co-therapies, partially or completely, in place of other conventional anti-inflammatory therapies, such as together with steroids, NSAIDs, COX-2 selective inhibitors, matrix metalloproteinase inhibitors, 5-lipoxygenase inhibitors, $LTB_4$ antagonists and $LTA_4$ hydrolase inhibitors.

Other conditions in which the compounds of the present invention will provide an advantage in inhibiting NO inhibition include cardiovascular ischemia, diabetes (type I or type II), congestive heart failure, myocarditis, atherosclerosis, migraine, glaucoma, aortic aneurysm, reflux esophagitis, diarrhea, irritable bowel syndrome, cystic fibrosis, emphysema, asthma, bronchiectasis, hyperalgesia (allodynia), cerebral ischemia (both focal ischemia, thrombotic stroke and global ischemia (for example, secondary to cardiac arrest), multiple sclerosis and other central nervous system disorders mediated by NO, for example Parkinson's disease. Further neurodegenerative disorders in which NO inhibition may be useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia, such as, for example pre-senile dementia, and AIDS-related dementia, cachexia, Sydenham's chorea, Huntington's disease, Amyotrophic Lateral Sclerosis, Korsakoff's disease, imbecility relating to a cerebral vessel disorder, sleeping disorders, schizophrenia, depression, depression or other symptoms associated with Premenstrual Syndrome (PMS), anxiety and septic shock.

Still other disorders or conditions which will be advantageously treated by the compounds of the present invention include treatment of prevention of opiate tolerance in patients needing protracted opiate analgesics, and benzodiazepine tolerance in patients taking benzodiazepines, and other addictive behavior, for example, nicotine addiction, alcoholism, and eating disorders. The compounds and methods of the present invention will also be useful in the treatment or prevention of drug withdrawal symptoms, for example treatment or prevention of symptoms of withdrawal from opiate, alcohol, or tobacco addiction. The present inventive compounds may also be useful to prevent tissue damage when therapeutically combined with antibacterial or antiviral agents.

The compounds of the present invention will also be useful in inhibiting NO production from L-arginine including systemic hypotension associated with septic and/or toxic hemorrhagic shock induced by a wide variety of agents; therapy with cytokines such as TNF, IL-1 and IL-2; and as an adjuvant to short term immunosuppression in transplant therapy.

Compounds of the invention are useful for the prevention or treatment of cancer, such as colorectal cancer, and cancer of the breast, lung, prostate, bladder, cervix and skin. The present invention is further directed to the use of the compounds of the present invention for the treatment and prevention of neoplasias. The neoplasias that will be treatable or preventable by the compounds and methods of the present invention include brain cancer, bone cancer, a leukemia, such as, for example chronic lymphocytic leukemia, a lymphoma, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, urogenital cancers, such as ovary cancer, cervical cancer, vulvar cancer, and lung cancer, breast cancer and skin cancer, such as squamous cell, melanoma, and basal cell cancers, prostate cancer, renal cell carcinoma, and other known cancers that effect epithelial cells throughout the body. Compounds of the present invention will be effective as well for treatment of mesenchymal derived neoplasias. Preferably, the neoplasia to be treated is selected from gastrointestinal cancer, liver cancer, bladder cancer, pancreas cancer, ovary cancer, prostate cancer, cervical cancer, vulvar cancer, lung cancer, breast cancer and skin cancer, such as squamous cell and basal cell cancers. The present compounds and methods can also be used to treat the fibrosis which occurs with radiation therapy. The present compounds and methods can be used to treat subjects having adenomatous polyps, including those with familial adenomatous polyposis (FAP). Additionally, the present compounds and methods can be used to prevent polyps from forming in patients at risk of FAP.

Conjunctive treatment of a compound of the present invention with another antineoplastic agent will produce a synergistic effect or alternatively reduce the toxic side effects associated with chemotherapy by reducing the therapeutic dose of the side effect-causing agent needed for therapeutic efficacy or by directly reducing symptoms of toxic side effects caused by the side effect-causing agent. A compound of the present invention will further be useful as an adjunct to radiation therapy to reduce side effects or enhance efficacy. In the present invention, another agent which can be combined therapeutically with a compound of the present invention includes any therapeutic agent which is capable of inhibiting the enzyme cyclooxygenase-2 ("COX-2"). Preferably such COX-2 inhibiting agents inhibit COX-2 selectively relative to the enzyme cyclooxygenase-1 ("COX-1"). Such a COX-2 inhibitor is known as a "COX-2 selective inhibitor". More preferably, a compound of the present invention can be therapeutically combined with a COX-2 selective inhibitor wherein the COX-2 selective inhibitor selectively inhibits COX-2 at a ratio of at least 10:1 relative to inhibition of COX-1, more preferably at least 30:1, and still more preferably at least 50:1 in an in vitro test. COX-2 selective inhibitors useful in therapeutic combination with the compounds of the present invention include celecoxib, valdecoxib, deracoxib, etoricoxib, rofecoxib, ABT-963 (2-(3,4-difluorophenyl)-4-(3-hydroxy-3-methyl-1-butoxy)-5-[4-(methylsulfonyl)phenyl-3(2H)-pyridazinone; described in PCT Patent Application No. WO 00/24719), or meloxicam. A compound of the present invention can also be advantageously used in therapeutic combination with a prodrug of a COX-2 selective inhibitor, for example parecoxib.

Another chemotherapeutic agent which will be useful in combination with a compound of the present invention can be selected, for example, from the following non-comprehensive and non-limiting list:

Alpha-difluoromethylornithine (DFMO), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19–384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, trimelamol, Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181–2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 zorubicin, alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-4048 1, Vestar boron-10, bromofosfamide, Wellcome BW-502, Wellcome BW-773, caracemide, carmethizole hydrochloride, Ajinomoto CDAF, chlorsulfaquinoxalone, Chemex CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tubular EMPTY, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, uroguanylin, combretastatin, dolastatin, idarubicin, epirubicin, estramustine, cyclophosphamide, 9-amino-2-(S)-camptothecin, topotecan, irinotecan (Camptosar), exemestane, decapeptyl (tryptorelin), or an omega-3 fatty acid.

Examples of radioprotective agents which may be used in a combination therapy with the compounds of this invention include AD-5, adchnon, arnifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

The compounds of the present invention will also be useful in treatment or prevention of angiogenesis-related disorders or conditions, for example, tumor growth, metastasis, macular degeneration, and atherosclerosis.

In a further embodiment, the present invention also provides therapeutic combinations for the treatment or prevention of ophthalmic disorders or conditions such as glaucoma. For example the present inventive compounds advantageously will be used in therapeutic combination with a drug which reduces the intraocular pressure of patients afflicted with glaucoma. Such intraocular pressure-reducing drugs include without limitation; latanoprost, travoprost, bimatoprost, or unoprostol. The therapeutic combination of a compound of the present invention plus an intraocular pressure-reducing drug will be useful because each is believed to achieve its effects by affecting a different mechanism.

In another combination of the present invention, the present inventive compounds can be used in therapeutic combination with an antihyperlipidemic or cholesterol-lowering drug such as a benzothiepine or a benzothiazepine antihyperlipidemic drug. Examples of benzothiepine antihyperlipidemic drugs useful in the present inventive therapeutic combination can be found in U.S. Pat. No. 5,994,391, herein incorporated by reference. Some benzothiazepine antihyperlipidemic drugs are described in WO 93/16055. Alternatively, the antihyperlipidemic or cholesterol-lowering drug useful in combination with a compound of the present invention can be an HMG Co-A reductase inhibitor. Examples of HMG Co-A reductase inhibitors useful in the present therapeutic combination include, individually, benfluorex, fluvastatin, lovastatin, provastatin, simvastatin, atorvastatin, cerivastatin, bervastatin, ZD-9720 (described in PCT Patent Application No. WO 97/06802), ZD-4522 (CAS No. 147098-20-2 for the calcium salt; CAS No. 147098-18-8 for the sodium salt; described in European Patent No. EP 521471), BMS 180431 (CAS No. 129829-03-4), or NK-104 (CAS No. 141750-63-2). The therapeutic combination of a compound of the present invention plus an antihyperlipidemic or cholesterol-lowering drug will be useful, for example, in reducing the risk of formation of atherosclerotic lesions in blood vessels. For example, atherosclerotic lesions often initiate at inflamed sites in blood vessels. It is established that antihyperlipidemic or cholesterol-lowering drug reduce risk of formation of atherosclerotic lesions by lowering lipid levels in blood. Without limiting the invention to a single mechanism of action, it is believed that one way the compounds of the present combination will work in concert to provide improved control of atherosclerotic lesions by, for example, reducing inflammation of the blood vessels in concert with lowering blood lipid levels.

In another embodiment of the invention, the present compounds can be used in combination with other compounds or therapies for the treatment of central nervous conditions or disorders such as migraine. For example, the present compounds can be used in therapeutic combination with caffeine, a 5-HT-1B/1D agonist (for example, a triptan such as sumatriptan, naratriptan, zolmitriptan, rizatriptan, almotriptan, or frovatriptan), a dopamine D4 antagonist (e.g., sonepiprazole), aspirin, acetaminophen, ibuprofen, indomethacin, naproxen sodium, isometheptene, dichloralphenazone, butalbital, an ergot alkaloid (e.g., ergotamine, dihydroergotamine, bromocriptine, ergonovine, or methyl ergonovine), a tricyclic antidepressant (e.g., amitriptyline or nortriptyline), a serotonergic antagonist (e.g., methysergide or cyproheptadine), a beta-andrenergic antagonist (e.g., propranolol, timolol, atenolol, nadolol, or metprolol), or a monoamine oxidase inhbitor (e.g., phenelzine or isocarboxazid). A further embodiment provides a therapeutic combination of a compound of the present invention with an opioid compound. Opioid compounds useful in this combination include without limitation morphine, methadone, hydromorphone, oxymorphone, levorphanol, levallorphan, codeine,dihydrocodeine, dihydrohydroxycodeinone, pentazocine, hydrocodone, oxycodone, nalmefene, etorphine, levorphanol, fentanyl, sufentanil, DAMGO, butorphanol, buprenorphine, naloxone, naltrexone, CTOP, diprenorphine, beta-funaltrexamine, naloxonazine, nalorphine, pentazocine, nalbuphine, naloxone benzoylhydrazone, bremazocine, ethylketocyclazocine, U50,488, U69,593, spiradoline, norbinaltorphimine, naltrindole, DPDPE, [D-la$^2$, glu$^4$] deltorphin, DSLET, met-enkephalin, leu-enkaphalin, beta-endorphin, dynorphin A, dynorphin B, and alpha-neoendorphin. An advantage to the combination of the present invention with an opioid compound is that the present inventive compounds will allow a reduction in the dose of the opioid compound, thereby reducing the risk or severity of opioid side effects, such as opioid addiction.

The term "alkyl", alone or in combination, means an acyclic alkyl radical, linear or branched, preferably containing from 1 to about 10 carbon atoms, more preferably containing from 1 to about 6 carbon atoms, and still more preferably about 1 to 3 carbon atoms. "Alkyl" also encompasses cyclic alkyl radicals containing from 3 to about 7 carbon atoms, preferably from 3 to 5 carbon atoms. Said alkyl radicals can be optionally substituted with groups as defined below. Examples of such radicals include methyl, ethyl, chloroethyl, hydroxyethyl, n-propyl, isopropyl, n-butyl, cyanobutyl, isobutyl, sec-butyl, tert-butyl, pentyl, aminopentyl, iso-amyl, hexyl, octyl and the like.

The term "alkenyl" refers to an unsaturated, acyclic hydrocarbon radical, linear or branched, in so much as it contains at least one double bond. Such radicals containing from 2 to about 6 carbon atoms, preferably from 2 to about 4 carbon atoms, more preferably from 2 to about 3 carbon atoms. Said alkenyl radicals may be optionally substituted with groups as defined below. Examples of suitable alkenyl radicals include propenyl, 2-chloropropylenyl, buten-1-yl, isobutenyl, penten-1-yl, 2-methylbuten-1-yl, 3-methylbuten-1-yl, hexen-1-yl, 3-hydroxyhexen-1-yl, hepten-1-yl, and octen-1-yl, and the like.

The term "alkynyl" refers to an unsaturated, acyclic hydrocarbon radical, linear or branched, in so much as it contains one or more triple bonds, such radicals containing 2 to about 6 carbon atoms, preferably from 2 to about 4 carbon atoms, more preferably from 2 to about 3 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "alkoxy" embrace linear or branched oxy-containing radicals each having alkyl portions of 1 to about 6 carbon atoms, preferably 1 to about 3 carbon atoms, such as a methoxy radical. The term "alkoxyalkyl" also embraces alkyl radicals having one or more alkoxy radicals attached to the alkyl radical, that is, to form monoalkoxyalkyl and dialkoxyalkyl radicals. Examples of such radicals include methoxy, ethoxy, propoxy, butoxy and tert-butoxy alkyls. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylthio" embraces radicals containing a linear or branched alkyl radical, of 1 to about 6 carbon atoms, attached to a divalent sulfur atom. An example of "lower alkylthio" is methylthio ($CH_3$—S—).

The term "alkylthioalkyl" embraces alkylthio radicals, attached to an alkyl group. Examples of such radicals include methylthiomethyl.

The term "halo" means halogens such as fluorine, chlorine, bromine or iodine atoms.

The term "heterocyclyl" means a saturated or unsaturated mono- or multi-ring carbocycle wherein one or more carbon atoms is replaced by N, S, P, or O. This includes, for example, the following structures:

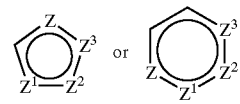

wherein Z, $Z^1$, $Z^2$ or $Z^3$ is C, S, P, O, or N, with the proviso that one of Z, $Z^1$, $Z^2$ or $Z^3$ is other than carbon, but is not O or S when attached to another Z atom by a double bond or when attached to another O or S atom. Furthermore, the optional substituents are understood to be attached to Z, $Z^1$, $Z^2$ or $Z^3$ only when each is C. The term "heterocyclyl" also includes fully saturated ring structures such as piperazinyl, dioxanyl, tetrahydrofuranyl, oxiranyl, aziridinyl, morpholinyl, pyrrolidinyl, piperidinyl, thiazolidinyl, and others. The term "heterocyclyl" also includes partially unsaturated ring structures such as dihydroflranyl, pyrazolinyl, imidazolinyl, pyrrolinyl, chromanyl, dihydrothiophenyl, and others.

The term "heteroaryl" means a fully unsaturated heterocycle.

In either "heterocycle" or "heteroaryl," the point of attachment to the molecule of interest can be at the heteroatom or elsewhere within the ring.

The term "cycloalkyl" means a mono- or multi-ringed carbocycle wherein each ring contains three to about seven carbon atoms, preferably three to about five carbon atoms. Examples include radicals such as cyclopropyl, cyclobutyl, cyclopentyl, cyclohexyl, cycloalkenyl, and cycloheptyl. The term "cycloalkyl" additionally encompasses spiro systems.

The term "oxo" means a doubly bonded oxygen.

The term "alkoxy" means a radical comprising an alkyl radical that is bonded to an oxygen atom, such as a methoxy radical. More preferred alkoxy radicals are "lower alkoxy" radicals having one to about ten carbon atoms. Still more preferred alkoxy radicals have one to about six carbon atoms. Examples of such radicals include methoxy, ethoxy, propoxy, isopropoxy, butoxy and tert-butoxy.

The term "aryl" means a fully unsaturated mono- or multi-ring carbocycle, including, but not limited to, substituted or unsubstituted phenyl, naphthyl, or anthracenyl.

The term "combination therapy" means the administration of two or more therapeutic agents to treat a therapeutic condition or disorder described in the present disclosure, for example atherosclerosis, pain, inflammation, migraine, neoplasia, angiogenisis-related condition or disorder, or other. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to include and qualify a combined amount of active ingredients in a combination therapy. This combined amount will achieve the goal of ameliorating the symptoms of, reducing or eliminating the targeted condition.

In one embodiment of the present invention, the compounds are represented by Formula I, II or III

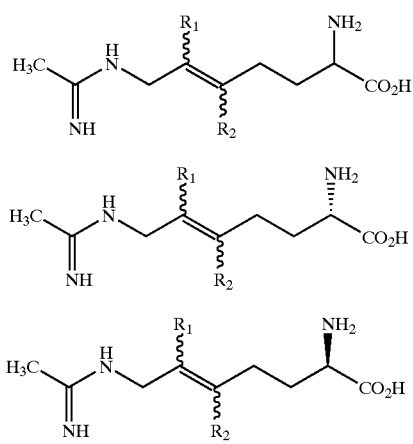

or a pharmaceutically acceptable salt thereof, wherein:
$R_1$ is H or methyl;
$R_2$ is H or methyl.

In another embodiment of Formula I, II or III, the compounds are represented wherein:
$R_1$ is H; and
$R_2$ is H or methyl.

In another embodiment of Formula I, II or III, the compounds are represented wherein:
$R_1$ is H; and
$R_2$ is methyl.

In another embodiment the compounds are represented by Formula I, II or III wherein:
$R_1$ is H; and
$R_2$ is H.

Formula I, II or III may also be represented wherein:
$R_1$ is methyl; and
$R_2$ is H or methyl.

Another embodiment of the invention is Formula I, II or III wherein:

$R_1$ is methyl; and
$R_2$ is H.

The compounds of Formula I, II or III may also be represented wherein:
$R_1$ is methyl; and
$R_2$ is methyl.

The compounds may also be represented wherein:
$R_1$ is H or methyl; and
$R_2$ is H.

In addition, the present invention contemplates the E and Z isomers of Formula I, II, and III within the intended scope.

Methods of using the compounds of Formula I, II and III include the use of inhibiting nitric oxide synthesis in a subject in need of such inhibition by administering a therapeutically effective amount of the present compound, selectively inhibiting nitric oxide synthesis produced by inducible nitric oxide synthase over nitric oxide produced by the constitutive forms of nitric oxide synthase in a subject in need of such inhibition by administering a therapeutically effective amount of a compound of Formula I, II or III, lowering nitric oxide levels in a subject in need of such by administering a therapeutically effective amount of a compound of Formula I, II or III, lowering nitric oxide levels in a subject in need of such by administering a therapeutically effective amount of a pharmaceutical composition comprising a compound of Formula I, II or III.

Also included in the family of compounds of Formula I, II or III are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of Formula I, II or III may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of Formula I, II or III include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compound of Formula I, II or III by reacting, for example, the appropriate acid or base with the compound of Formula I, II or III.

While it may be possible for the compounds of Formula I, II or III to be administered as the raw chemical, it is preferable to present them as a pharmaceutical composition. According to a further aspect, the present invention provides a pharmaceutical composition comprising a compound of Formula I, II or III or a pharmaceutically acceptable salt or solvate thereof, together with one or more pharmaceutically acceptable carriers thereof and optionally one or more other therapeutic ingredients. The carrier(s) must be acceptable in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of Formula I, II or III or a pharmaceutically acceptable salt or solvate thereof with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a nonaqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 0.5 mg to 200 mg, usually around 0.5 mg to 100 mg.

The compounds of Formula I, II or III are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

Compounds of the present invention can exist in tautomeric, geometric or stereoisomeric forms. The present invention contemplates all such compounds, including cis- and trans-geometric isomers and mixtures thereof, E- and Z-geometric isomers and mixtures thereof, R- and S-enantiomers, diastereomers, d-isomers, l-isomers, the racemic mixtures thereof and other mixtures thereof, as falling within the scope of the invention. Pharmaceutically acceptable salts of such tautomeric, geometric or stereoisomeric forms are also included within the invention.

The terms "cis" and "trans" denote a form of geometric isomerism in which two carbon atoms connected by a double bond will each have two highest ranking groups on the same side of the double bond ("cis" or "Z") or on opposite sides of the double bond ("trans" or "E"). Some of the compounds described contain alkenyl groups, and are meant to include both cis and trans or "E" and "Z" geometric forms. Other compounds of the invention include mixtures of both the cis/Z and the trans/E isomers.

Some of the compounds described contain one or more stereocenters and are meant to include R, S, and mixtures of R and S forms for each stereocenter present. Some of the compounds described contain one or more geometric isomers and are meant to include E, Z and mixtures of E and Z forms for each stereocenter present.

Scheme 1A

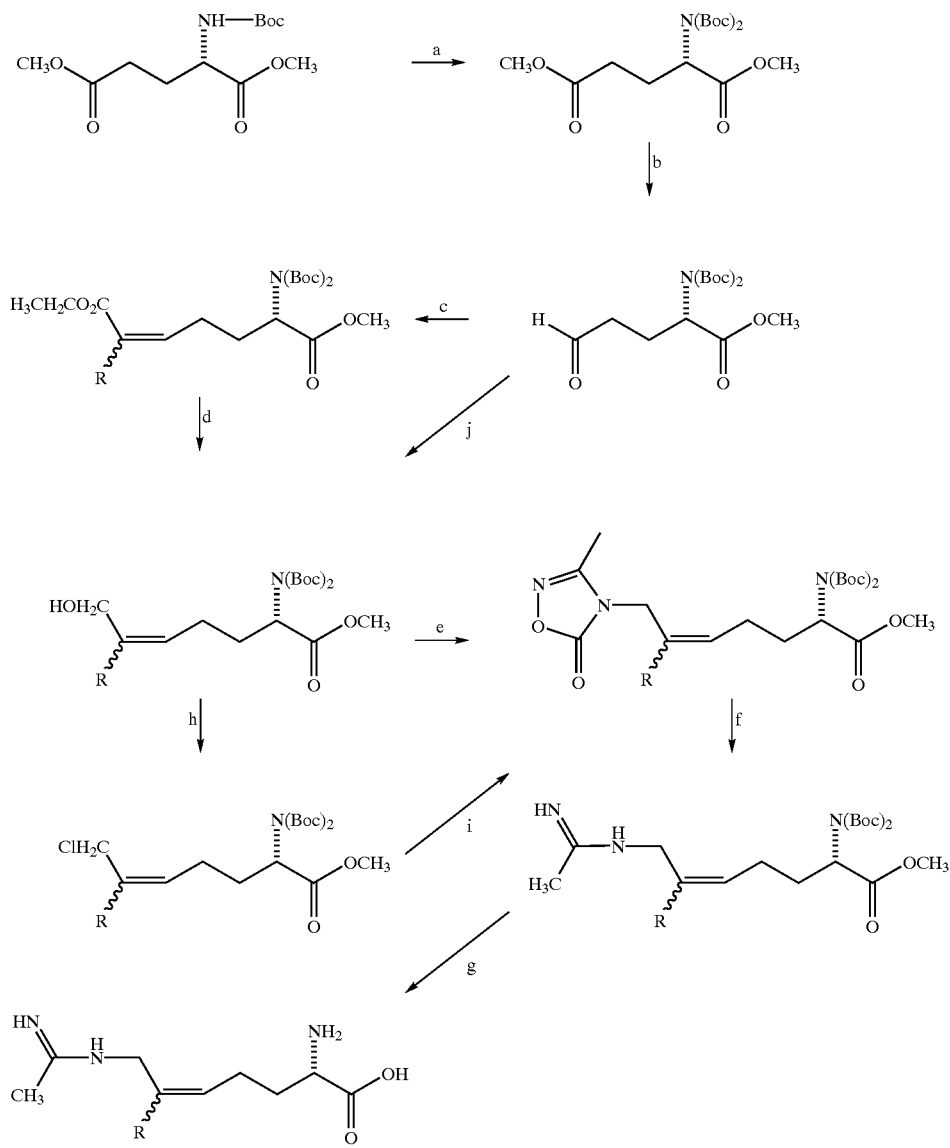

R = H, CH₃
a) di-tert-butyldicarbonate, 4-dimethylaminopyridine, acetonitrile
b) DIBAL, hexane and diethyl ether
c) triethyl phosphonoacetate or triethyl phosphonopropionate
e) polymer-supported triphenylphosphine, 3-methyl-1,2,4-oxadiazolin-5-o ne, dimethylazodicarboxylate, THF
f) Zinc dust, methanol, acetic acid, water, sonication
g) aqueous HCl, heat
h) methane sulfonyl chloride, base
i) 3-methyl-1,2,4,-oxadiazolin-5-one, base
j) 1) O-TBDMS-triphenylphosphonium ethanol, base, THF and hexane
   2) TBAF Scheme 1B

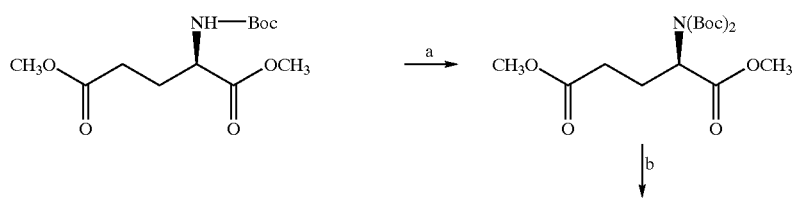

-continued

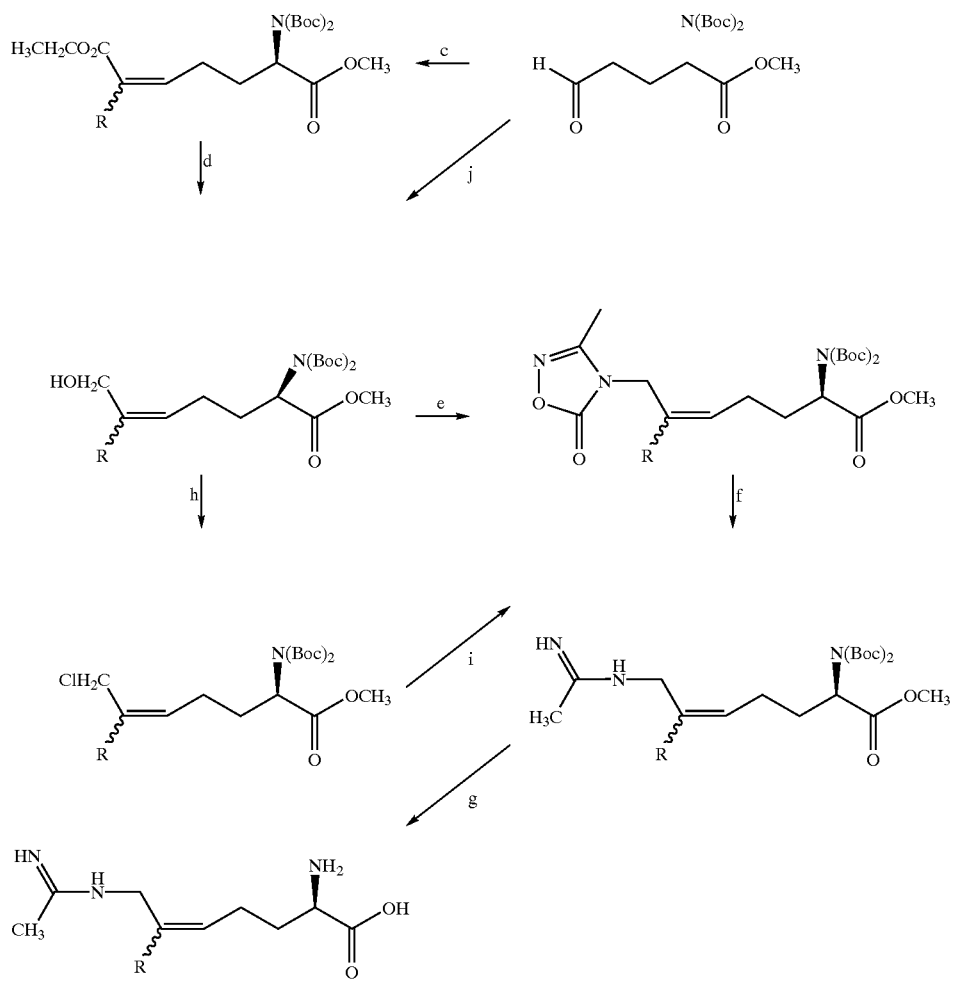

R = H, CH₃
a) di-tert-butyldicarbonate, 4-dimethylaminopyridine, acetonitrile
b) DIBAL, hexane and diethyl ether
c) triethyl phosphonoacetate or triethyl phosphonopropionate
e) polymer-supported triphenylphosphine, 3-methyl-1,2,4-oxadiazolin-5-o ne, dimethylazodicarboxylate, THF
f) Zinc dust, methanol, acetic acid, water, sonication
g) aqueous HCl, heat
h) methane sulfonyl chloride, base
i) 3-methyl-1,2,4,-oxadiazolin-5-one, base
j) 1) O-TBDMS-triphenylphosphonium ethanol, base, THF and hexane
   2) TBAF Scheme 2

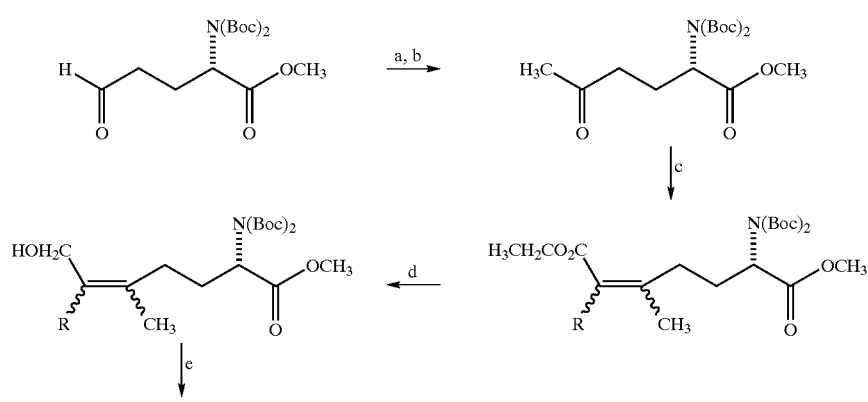

-continued

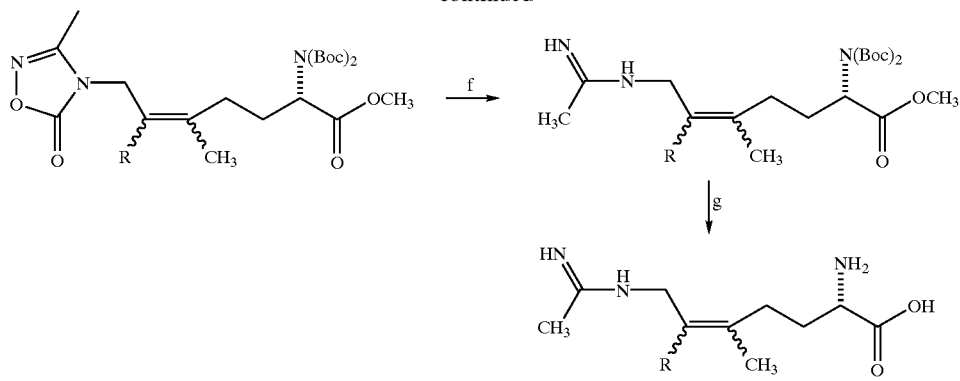

R = H, CH₃
a) methyl Grignard, THF
b) N-methylmorpholine-N-oxide, tetra-n-propylammonium perruthenate, methylene chloride
c) triethyl phosphonoacetate or triethyl phosphonopropionate, n-butyl lithium, THF and hexane
d) NaBH₄, methanol
e) polymer-supported triphenylphosphine, 3-methyl-1,2,4-oxadiazolin-5-one, dimethylazodicarboxylate, THF
f) Zinc dust, methanol, acetic acid, water, sonication
g) aqueous HCl, heat The following examples can be made using the preceding synthetic schemes and are provided to illustrate the present invention and not intended to limit the scope thereof. Those skilled in the art will readily understand that known variations of the conditions and processes of the preparative procedures can be used to prepare these compounds.

The following general synthetic sequences are useful in making the present invention.

Scheme 1A

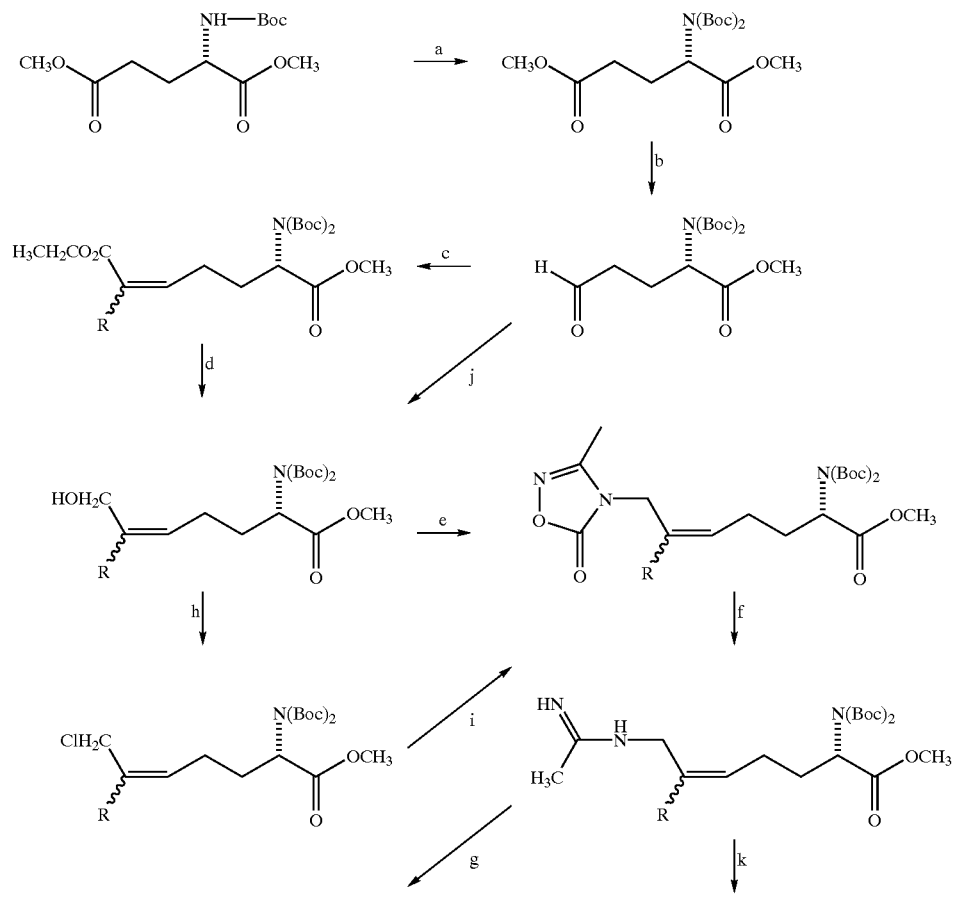

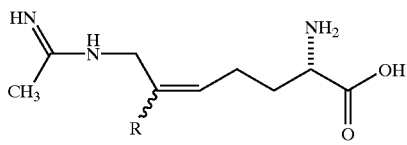
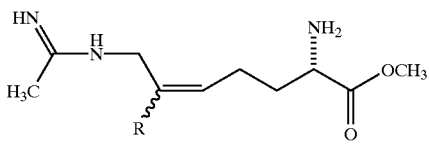

R = H, CH₃ a) di-tert-butyldicarbonate, 4-dimethylaminopyridine, acetonitrile
b) DIBAL, hexane and diethyl ether
c) triethyl phosphonoacetate or triethyl phosphonopropionate
e) polymer-supported triphenylphosphine, 3-methyl-1,2,4-oxadiazolin-5-one, dimethylazodicarboxylate, THF
f) Zinc dust, methanol, acetic acid, water, sonication
g) aqueous HCl, heat
h) methane sulfonyl chloride, base
i) potassium 3-methyl-1,2,4,-oxadiazolin-5-one, DMF, 50° C.
j) 1) O-TBDMS-triphenylphosphonium ethanol, base, THF and hexane
   2) TBAF
k) HCl Scheme 1B

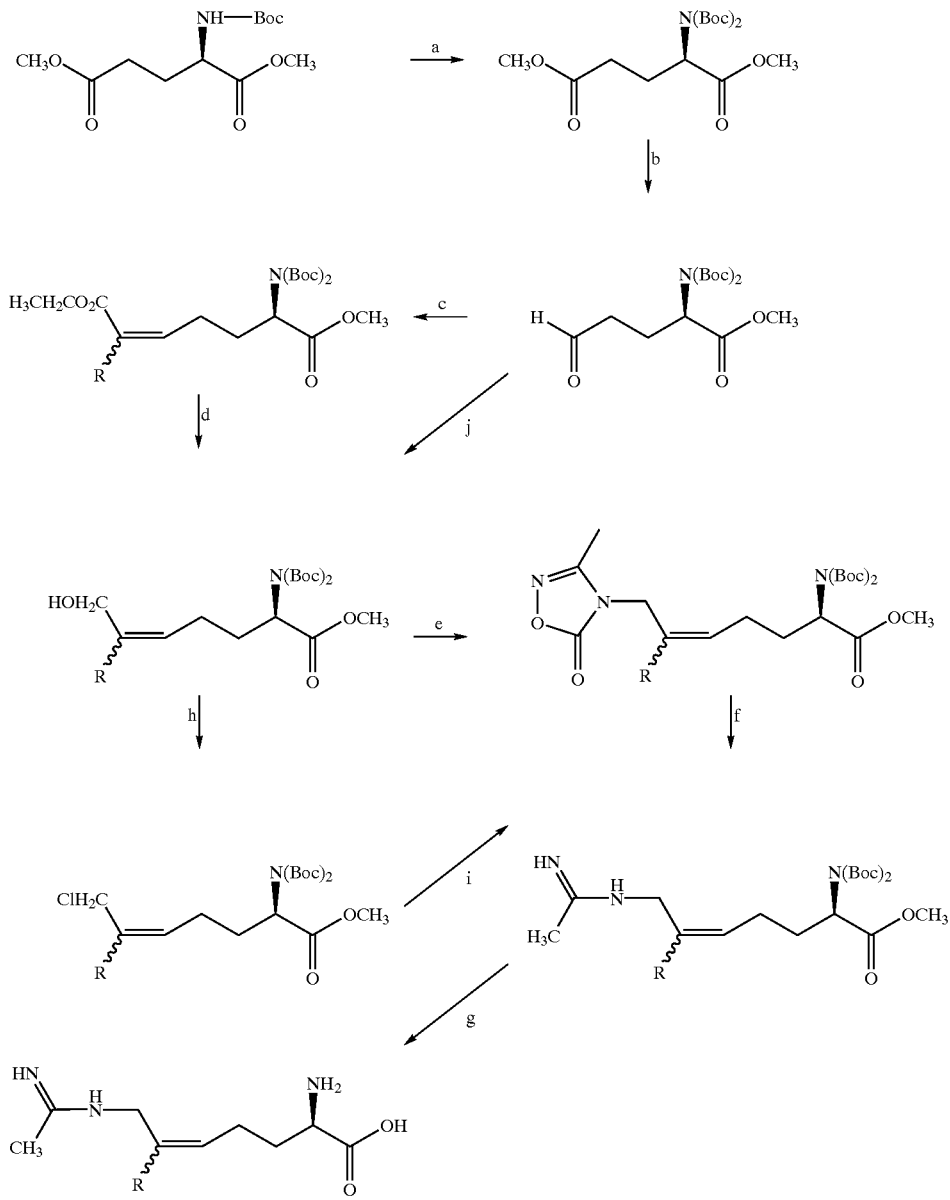

-continued

R = H, CH₃
a) di-tert-butyldicarbonate, 4-dimethylaminopyridine, acetonitrile
b) DIBAL, hexane and diethyl ether
c) triethyl phosphonoacetate or triethyl phosphonopropionate
e) polymer-supported triphenylphosphine, 3-methyl-1,2,4-oxadiazolin-5-o ne, dimethylazodicarboxylate, THF
f) Zinc dust, methanol, acetic acid, water, sonication
g) aqueous HCl, heat
h) methane sulfonyl chloride, base
i) potassium 3-methyl-1,2,4,-oxadiazolin-5-one, DMF, 50° C.
j) 1) O-TBDMS-triphenylphosphonium ethanol, base, THF and hexane
   2) TBAF Scheme 1C

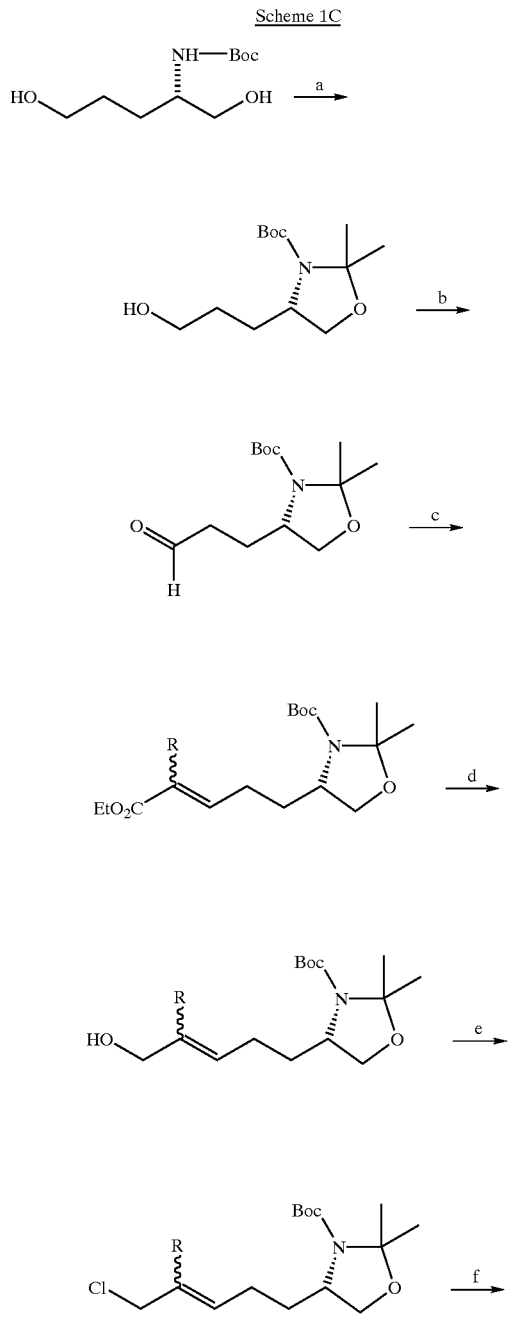

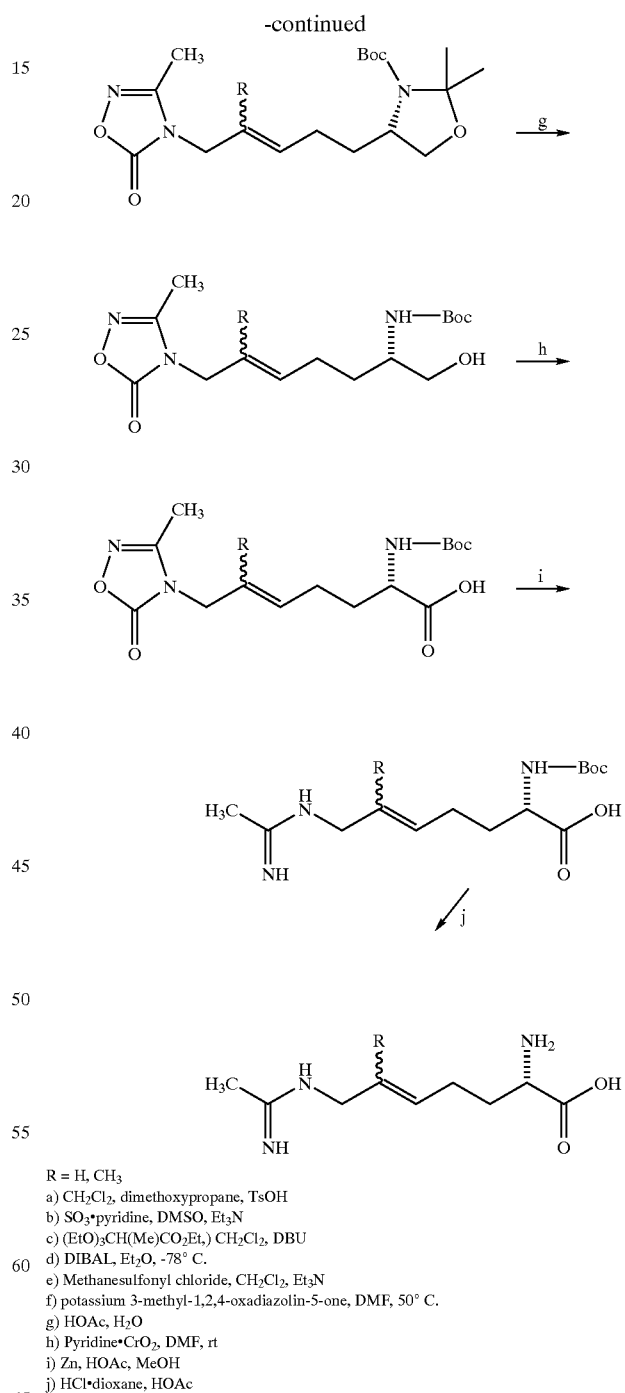

R = H, CH₃
a) CH₂Cl₂, dimethoxypropane, TsOH
b) SO₃•pyridine, DMSO, Et₃N
c) (EtO)₃CH(Me)CO₂Et,) CH₂Cl₂, DBU
d) DIBAL, Et₂O, -78° C.
e) Methanesulfonyl chloride, CH₂Cl₂, Et₃N
f) potassium 3-methyl-1,2,4-oxadiazolin-5-one, DMF, 50° C.
g) HOAc, H₂O
h) Pyridine•CrO₂, DMF, rt
i) Zn, HOAc, MeOH
j) HCl•dioxane, HOAc Scheme 2

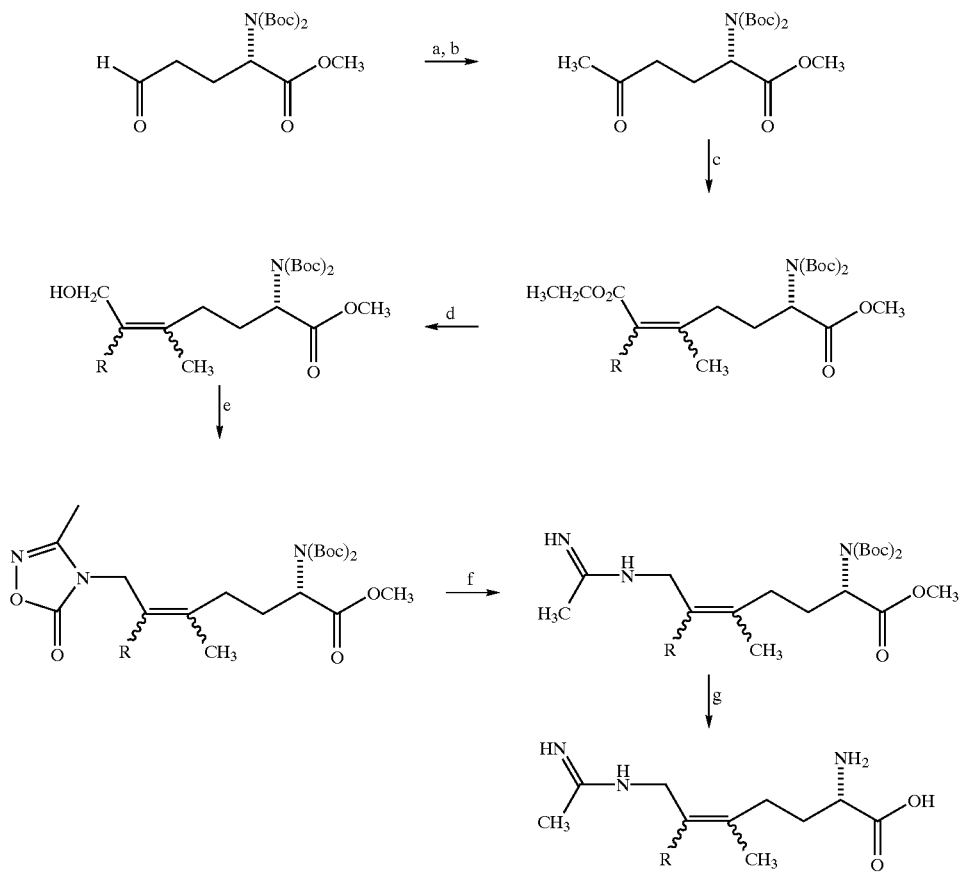

R = H, CH3
a) methyl Grignard, THF
b) N-methylmorpholine-N-oxide, tetra-n-propylammonium perruthenate, methylene chloride
c) triethyl phosphonoacetate or triethyl phosphonopropionate, n-butyl lithium, THF and hexane
d) NaBH4, methanol
e) polymer-supported triphenylphosphine, 3-methyl-1,2,4-oxadiazolin-5-one, dimethylazodicarboxylate, THF
f) Zinc dust, methanol, acetic acid, water, sonication
g) aqueous HCl, heat The following examples can be made using the preceding synthetic schemes and are provided to illustrate the present invention and not intended to limit the scope thereof. Those skilled in the art will readily understand that known variations of the conditions and processes of the preparative procedures can be used to prepare these compounds.

EXAMPLE 1

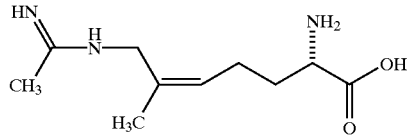

(2S,5Z)-2-amino-6-methyl-7-[(1-iminoethyl)amino]-5-heptenoic acid, dihydrochloride

EXAMPLE 1a

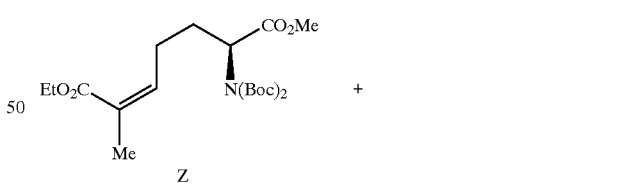

A solution of triethyl-2-phosphonopropionate (6.5 mg, 27.1 mmol) in toluene (60 ML) was treated with 0.5 M potassium bis(trimethylsilyl) amide (50.0 ML, in toluene) and the resulting anion was condensed with the aldehyde product of Example 8c by the method of Example 8d. This produced, after chromatography, 8 g of a 3:7 mixture respectively of the desired Z and E diesters.

(¹H)NMR (300 MHz, CDCl3) 6.7–6.8 ppm (m, 1H), 5.9 ppm (m, 1H), 4.9 ppm (m, 1H), 4.2 ppm (q, 2H), 3.7 ppm (s, 3H), 2.5 ppm (m, 1H), 2.2–2.3 ppm (m, 2H), 2.0 ppm (m, 1H), 1.9 ppm (s, 3H), 1.8 ppm (s, 3H), 1.5 ppm (s, 18H), 1.3 ppm (t, 3H).

EXAMPLE 1b

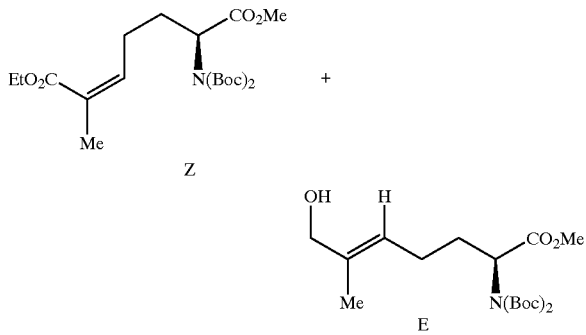

The product mixture of Example 1a (850 mg, 2.0 mmol) in Et$_2$O (30 mL) was reduced over a period of twenty minutes with diisobutyl aluminum/hydride (DIBAL) by the method of Example 8e to produce the crude illustrated desired mixture of E-alcohol and unreduced Z-ester. This mixture was chromatographed on silica gel eluting with n-hexane:EtOAc (9:1) to n-hexane: EtOAc (1:1) providing samples of the Z-ester (530 mg) and the E-alcohol desired materials.

Z-ester: (¹H)NMR (300 MHz, CDCl3) 5.9 ppm (m, 1H), 4.9 ppm (m, 1H), 4.2 ppm (q, 2H), 3.7 ppm (s, 3H), 2.5 ppm (m, 1H), 2.2–2.3 ppm (m, 2H), 1.9 ppm (s, 3H), 1.5 ppm (s, 18H), 1.3 ppm (t, 3H).

E-alcohol: (¹H)NMR (300 MHz, CDCl3) 5.35 ppm (m, 1H), 4.9 ppm (m, 1H), 3.95 ppm (s, 1H), 3.7 ppm (s, 3H), 1.8–2.2 ppm (m, 6H), 1.6 ppm (s, 3H), 1.5 ppm (s, 18H).

EXAMPLE 1c

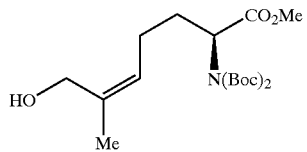

The product Z-ester of Example 1b (510 mg, 1.2 mmol) in Et$_2$O (30 ML) was reduced over a period of two hours with duisobutyl aluminum/hydride (DIBAL) by the method of Example 8e to produce the crude illustrated desired Z-alcohol. This material was chromatographed on silica gel eluting with n-hexane:EtOAc (9:1) to n-hexane:EtOAc (8:2) to yield 340 mg of the desired Z-alcohol product.

(¹H)NMR (300 MHz, CDCl$_3$) δ5.3 ppm (m, 1H), 4.9 ppm (m, 1H), 4.2 ppm (d, 1H), 4.0 ppm (d, 1H), 2.2 ppm (m, 3H), 1.95 ppm (m, 1H), 1.8 ppm (s, 3H), 1.5 ppm (s, 18H).

EXAMPLE 1d

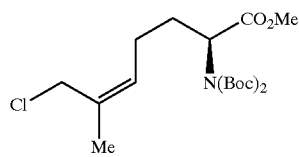

A CH$_2$Cl$_2$ solution (5 ML) of the product alcohol of Example 1c (340 mg, 0.9 mmol) was treated with triethylamine (151 mg, 1.5 mmol). To this solution cooled in an ice bath was added a CH$_2$Cl$_2$ solution (1.5 ML) of methanesulfonyl chloride. After fifteen minutes the ice bath was removed and the reaction was stirred at ambient temperature for 20 h. The reaction mixture was e then washed with 10% KHSO$_4$, dried over Na$_2$SO$_4$, and stripped of all solvent under reduced pressure to produce 350 mg of the desired Z-allylic chloride.

(¹H)NMR (300 MHz, CDCl$_3$) δ5.4 ppm (m, 1H), 4.9 ppm (m, 1H), 4.1 ppm (d, 1H), 4.0 ppm (d, 1H), 2.1 ppm (m, 3H), 1.95 ppm (m, 1H), 1.8 ppm (s, 3H), 1.5 ppm (s, 18H).

EXAMPLE 1e

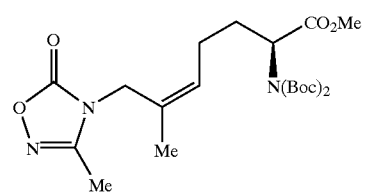

A suspension of potassium 3-methyl-1,2,4-oxa-diazoline-5-one in DMF is reacted with a DMF solution of the product of Example 1d by the method of Example 2b to produce the material.

EXAMPLE 1f

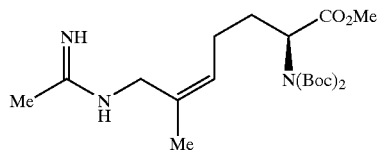

The product of Example 1e is reacted with zinc in HOAc by the method of Example 8g to yield the amidine.

EXAMPLE 1g

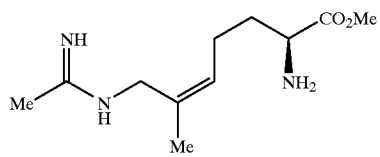

The product of Example 1f was reacted with 4NHCl in dioxane in glacial HOAc to yield the amidine.

EXAMPLE 1

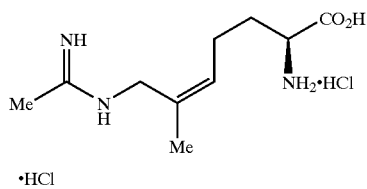

·HCl

The product of Example 1g is deprotected to yield the amino acid, dihydrochloride.

EXAMPLE 2

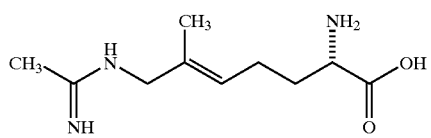

(2S,5E)-2-amino-6-methyl-7-[(1-iminoethyl)amino]-5-heptenoic acid, dihydrochloride

EXAMPLE 2a

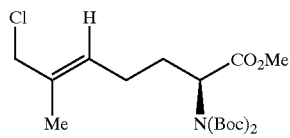

The E-alcohol product of Example 1b (1.3 g, 3.3 mmol) was reacted with triethylamine (525 mg, 5.2 mmol) and methanesulfonyl chloride (560 mg, 5.2 mmol) by the method of Example 1d to yield 1.4 g of the desired E-allylic chloride.

($^1$H)NMR (400 MHz, CDCl3) 5.5 ppm (m, 1H), 4.9 ppm (m, 1H), 4.0 ppm (s, 2H), 3.7 ppm (s, 3H), 2.1–2.3 ppm (m, 3H), 1.9 ppm (m, 1H), 1.7 ppm (s, 3H), 1.5 ppm (s, 18H).

EXAMPLE 2b

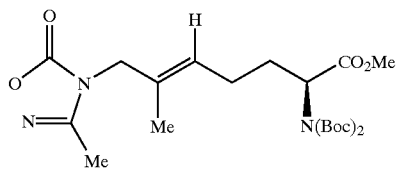

A suspension of potassium 3-methyl-1,2,4-oxa-diazoline-5-one (460 mg, 3.35 mmol) in 5 mL of DMF was treated with a DMF (15 mL) solution of the product of Example 2a. This reaction mixture was stirred at 50° C. for 17 h before an additional 50 mg (0.04 mmol) of the diazoline-5-one salt was added. Heating of the stirred reaction was continued for an additional 3 h before it was cooled to room temperature and diluted with 180 mL of water. This mixture was extracted with EtOAc and the extracts were diluted with 120 mL of n-hexane, washed with water, dried over Na$_2$SO$_4$ and stripped of all solvent under reduced pressure to yield 1.3 g of the material.

($^1$H)NMR (400 MHz, CDCl3) 5.5 ppm (m, 1H), 4.9 ppm (m, 1H), 4.2 ppm (s, 3H),3.7 ppm (s, 3H), 2.2 ppm (m, 3H), 1.95 ppm (m, 1H), 1.8 ppm (s, 3H), 1.5 ppm (s, 18H).

EXAMPLE 2c

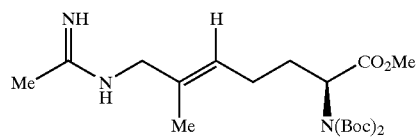

The product of Example 2b (460 mg, 1.0 mmol) was reacted with zinc in HOAc by the method of Example 8g to yield 312 mg of the desired amidine after HPLC purification.

EXAMPLE 2

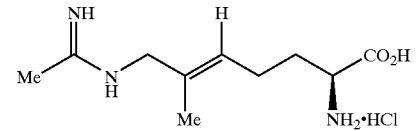

·HCl

The product of Example 2c (77 mg, 0.2 mmol) was deprotected with 2N HCl by the method of Example 8 to yield 63 mg the E-amino acid, dihydrochloride.

EXAMPLE 3

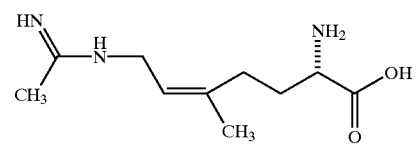

(2S,5Z)-2-amino-5,6-dimethyl-7-[(1-iminoethyl)amino]-5-heptenoic acid, dihydrochloride

EXAMPLE 4

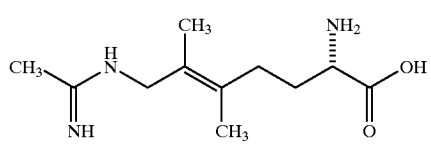

(2S,5Z)-2-amino-5-methyl-7-[(1-iminoethyl)amino]-5-heptenoic acid, dihydrochloride

EXAMPLE 5

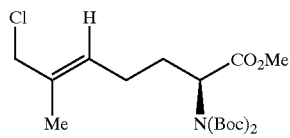

(2S,5E)-2-amino-5,6-dimethyl-7-[(1-iminoethyl)amino]-5-heptenoic acid, dihydrochloride

EXAMPLE 6

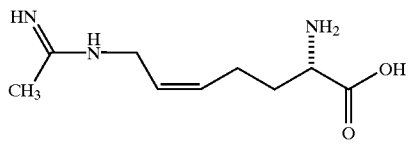

(2S,5Z)-2-amino-7-[(1-iminoethyl)amino]-5-heptenoic acid, dihydrochloride

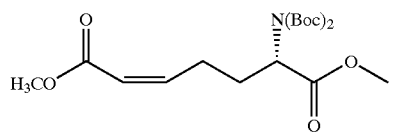

6a) Methyl bis(trifluoroethyl)phosphonoacetate (4.77 g, 15 mmol) and 23.7 g (90 mmol) of 18-crown-6 were dissolved in 80 mL of anhydrous THEF and cooled to −78° C. To this soution was added 30 mL (15 mmol) of potassium bis(trimethylsilyl) amide, followed by 5.1 g (14.7 mmol) of N,N-diBoc glutamic aldehyde methyl ester from Example 8c. After stirring for 30 minutes at −78° C., the reacion was quenched with aqueous $KHSO_4$. Extraction of the reaction mixture with EtOAc and concentration afforded 2.95 g (49%) of the desired compound. Mass spectra M+H=402.

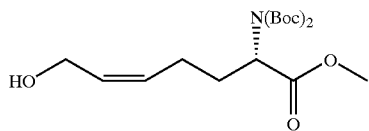

6b) The product from example 6a was reduced by the method of example 8e to afford the desired compound.

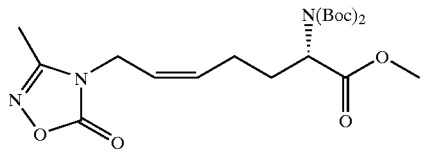

6c) The product from example 6b was allowed to react with 3-methyl-1,2,4-oxadiazolin-5-one by the method of example 8f to afford the desired compound.

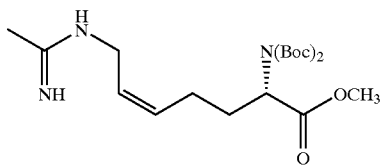

6d) The product from example 6c was deprotected by the method of example 8 g to afford the desired compound.

6) The product from example 6d was dissolved in 2 N HCl and heated at reflux. The reaction mixture was cooled and concentrated to afford 0.12 g of the desired product. $H^1$-NMR 1.8–2.0 (m, 2H); 2.05 (s, 3H); 2.15 (q, 2H); 3.75 (d, 2H); 3.9 (t, 1H); 5.4 (m, 1H); 5.6 (m, 1H)

EXAMPLE 7

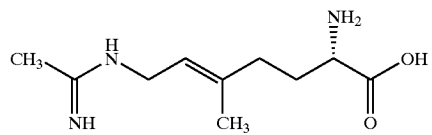

(2S,5E)-2-amino-5-methyl-7-[(1-iminoethyl)amino]-5-heptenoic acid, dihydro chloride

EXAMPLE 8

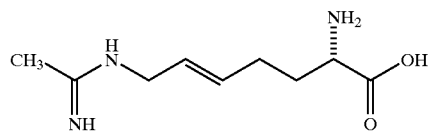

(2S,5E)-2-amino-7-[(1-iminoethyl)amino]-5-heptenoic acid, dihydrochloride

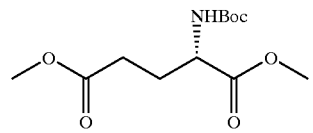

8a) L-glutamic acid (6.0 g, 40.78 mmol) was dissolved in methanol (100 mL). To the reaction mixture trimethylsilyl chloride (22.9 mL, 180 mmol) was added at 0° C. under nitrogen and allowed to stir overnight. To the reaction mixture at 0° C. under nitrogen triethylamine (37 mL, 256 mmol) and di-tert-butyldicarbonate (9.8 g, 44.9 mmol) was added and stirred two hours. The solvent was removed and the residue was triturated with ether (200 mL). The triturated mixture was filtered. The filtrate was evaporated to an oil and chromatographed on silica, eluting with ethyl acetate and hexane, to give the mono boc L-glutamic di ester (10.99 g, 98%).

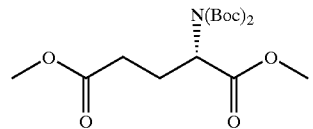

8b) Mono boc L-glutamic acid (10.95 g, 39.8 mmol) was dissolved in acetonitrile (130 mL). To the reaction mixture 4-dimethylaminopyridine (450 mg, 3.68 mmol) and di-tert-butyldicarbonate (14.45 g, 66.2 mmol) was added and stirred for 20 hours. The solvent was evaporated and the residue chromatographed on silica and eluting with ethyl acetate and hexane to give the di-boc-L-glutamic diester (14.63 g, 98%).

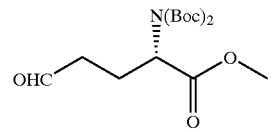

8c) The product from example 8b (10.79 g, 28.7 mmol) was dissolved in diethyl ether (200 mL) and cooled in a dry ice bath to −80 C. To the reaction mixture Diisobutylaluminum hydride (32.0 mL, 32.0 mmol) was added and stirred 25 minutes. The reaction mixture was removed from the dry ice bath and water (7.0 mL) was added. Ethyl acetate (200 mL) was added to the reaction mixture and stirred 20 minutes. Magnesium sulfate (10 g) was added to the reaction mixture and stirred 10 minutes. The reaction mixture was filtered through celite and concentrated to give a clear yellow oil (11.19 g). The yellow oil was chromatographed on silica and eluting with ethyl acetate and hexane. The product (8.61, 87%) was a clear light yellow oil.

Mass Spectrometry: M+H 346, M+Na 378

(¹H)NMR (400 MHz, CDCl₃) 9.74 ppm (s, 1H), 4.85 ppm (m, 1H), 3.69 ppm (s, 3H), 2.49 ppm (m, 3H), 2.08 ppm (m, 1H), 1.48 ppm (s, 18H).

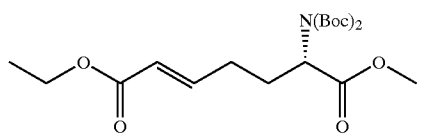

8d) Triethyl phosphonoacetate (6.2 mL, 31.2 mmol) was dissolved in toluene (30 mL) and placed in an ice bath under nitrogen and cooled to 0° C. To the reaction mixture, potassium bis(trimethylsilyl) amide (70 mL, 34.9 mmol) was added and stirred 90 minutes. To the reaction mixture the product from example 8c (8.51 g, 24.6 mmol) dissolved in toluene (20 mL) was added and stirred 1 hour. The reaction mixture was warmed to room temperature. To the reaction mixture Potassium hydrogen sulfate (25 mL, 25 mmol) was added and stirred 20 minutes. The mixture was extracted with ethyl acetate (3×100 mL), dried over Magnesium sulfate and concentrated to give a cloudy brownish yellow oil (12.11 g). The oil was chromatographed on silica, eluted with ethyl acetate and toluene to give a light yellow oil (7.21 g, 70%).

Mass Spectrometry: M+H 416, M+NH₄ 433, -boc 316, -2 boc, 216.

(¹H)NMR (400 MHz, CDCl₃) 6.88 ppm (m, 1H), 5.82 ppm (d, 1H), 4.81 ppm (m, 1H), 5.76 ppm (s, 3H), 2.50 ppm (m, 3H), 2.21 ppm (m, 1H), 1.45 ppm (s, 18H).

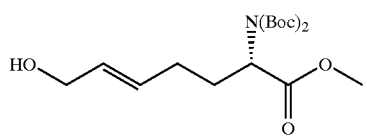

8e) The product from example 8d (5.0 g, 12.03 mmol) was dissolved in diethyl ether (100 mL) and placed in a dry ice bath and cooled to −80° C. To the reaction mixture was added diisobutylaluminum hydride (21.0 mL, 21.0 mmol). And stirred 30 minutes. To the reaction mixture water (10 mL) was added, removed from dry ice bath, and stirred 60 minutes. To the reaction mixture magnesium sulfate (10 g) was added and stirred 10 minutes. The reaction mixture was filtered over celite and concentrated to give a yellow oil (5.0 g). The oil was chromatographed on silica, eluted with ethyl acetate and hexane, to give a light yellow oil (2.14 g, 47%).

Mass Spectrometry: M+H 374, M+NH₄ 391

(¹H)NMR (400 MHz, CDCl₃) 5.63 ppm (m, 2H), 4.88 ppm (m, 1H), 4.02 ppm (s, 2H), 3.68 ppm (s, 3H), 2.12 ppm (m, 4H), 1.47 ppm (s, 18H).

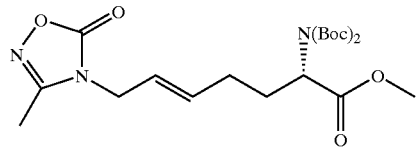

8f) The product from example 8e was dissolved in tetrahydrofuran (50 mL). To the reaction mixture triphenyl phosphine on polymer (3.00 g, 8.84 mmol), oxadiazolinone (720 mg, 7.23 mmol), and azodicarboxylic acid dimethyl ester (1.17 g, 3.21 mmol) were added and stirred six hours at room temperature. The reaction mixture was filtered over celite and concentrated to give a cloudy yellow oil (2.81 g). The oil was chromatographed on silica, eluting with ethyl acetate in hexane, to give a clear colorless oil (1.66 g, 68%).

Mass Spectrometry: M+H 456, M+NH₄473, -boc 356, -2 boc 256

(¹H)NMR (400 MHz, CDCl₃) 5.65 ppm (m, 1H), 5.45 ppm (m, 1H), 4.79 ppm (m, 1H), 4.11 ppm (d, 2H), 3.68 ppm (s, 3H), 2.17 ppm (m, 4H), 1.47 ppm (s, 18 H).

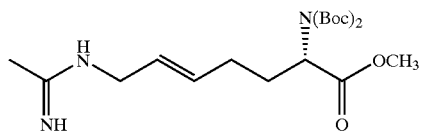

8g) Product from example 8f (300 mg, 0.66 mmol) was dissolved in a solution of acetic acid and water (10 mL, 25/75) containing zinc metal and sonicated for 3 hours. The reaction mixture was filtered over celite and chromatographed on reverse phase HPLC to give a clear colorless residue (13 mg, 4%).

(¹H)NMR (400 MHz, CDCl₃) 8.89 ppm (m, 1H), 5.68 ppm (m, 1H), 5.47 ppm (m, 1H), 3.80 ppm (d, 2H), 3.71 ppm (s, 3H), 2.18 ppm (m, 4H), 1.41 ppm (s, 18 H).

8) The product from example 8 g (13.0 mg, 0.031 mmol) was dissolved in 2 N HCl (1.22 mL, 2.44 mmol) and refluxed 1 hour. The reaction mixture was cooled, concentrated, to give a clear colorless oil (6.6 mg, 95%)

Mass Spectrometry: M+H 200, (¹H)NMR (400 MHz, D₂0) 5.65 ppm (m, 1H), 5.47 ppm (m, 1H), 3.80 ppm (t, 1H), 3.72 ppm (d, 2H), 2.0 ppm (m, 5H), 1.87 ppm (m, 2H).

EXAMPLE 9

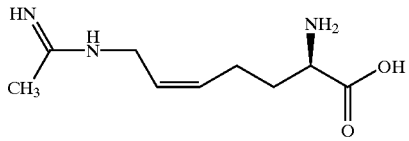

(2R,5Z)-2-amino-7-[(1-iminoethyl)amino]-5-heptenoic acid, dihydrochloride

EXAMPLE 10

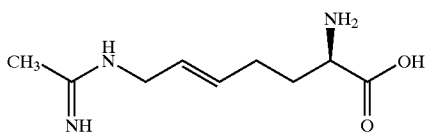

(2R,5E)-2-amino-7-[(1-iminoethyl)amino]-5-heptenoic acid, dihydrochloride

Biological Data

Some or all of the following assays are used to demonstrate the nitric oxide synthase inhibitory activity of the invention's compounds as well as demonstrate the useful pharmacological properties.

Rat Carrageenan Foot Pad Edema Test

The carrageenan foot edema test is a useful assay for evaluating anti-inflammaory properties of compounds of the present invention. The carrageenan foot edema test is performed with materials, reagents and procedures essentially as described by Winter, et al., (*Proc. Soc. Exp. Biol. Med.*, 111, 544 (1962)). Male Sprague-Dawley rats are selected in each group so that the average body weight is as close as possible. Rats are fasted with free access to water for over sixteen hours prior to the test. The rats are dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline is administered and the volume of the injected foot is measured with a displacement plethysmometer connected to a pressure transducer with a digital indicator. Three hours after the injection of the carrageenan, the volume of the foot is again measured. The average foot swelling in a group of drug-treated animals is compared with that of a group of placebo-treated animals and the percentage inhibition of edema is determined (Otterness and Bliven, *Laboratory Models for Testing NSAIDs, in Non-steroidal Anti-Inflammatory Drugs*, (J. Lombardino, ed. 1985)). The percent inhibition shows the percentage decrease from control paw volume determined in this procedure.

Citrulline Assay for Nitric Oxide Synthase

Nitric oxide synthase (NOS) activity can be measured by monitoring the conversion of L-[2,3-$^3$H]-arginine to L-[2,3-$^3$H]-citrulline (Bredt and Snyder, *Proc. Natl. Acad. Sci. U.S.A.*, 87, 682–685, 1990 and Moore et al, *J. Med. Chem.*, 39, 669–672, 1996). Human inducible NOS (hiNOS), human endothelial constitutive NOS (hecNOS) and human neuronal constitutive NOS (hncNOS) are each cloned from RNA extracted from human tissue. The cDNA for human inducible NOS (hiNOS) is isolated from a λcDNA library made from RNA extracted from a colon sample from a patient with ulcerative colitis. The cDNA for human endothelial constitutive NOS (hecNOS) is isolated from a λcDNA library made from RNA extracted from human umbilical vein endothelial cells (HUVEC) and the cDNA for human neuronal constitutive NOS (hncNOS) is isolated from a λcDNA library made from RNA extracted from human cerebellum obtained from a cadaver. The recombinant enzymes are expressed in Sf9 insect cells using a baculovirus vector (Rodi et al, in *The Biology of Nitric Oxide, Pt. 4: Enzymology. Biochemistry and Immunology;* Moncada, S., Feelisch, M., Busse, R., Higgs, E., Eds.; Portland Press Ltd.: London, 1995; pp 447–450). Enzyme activity is isolated from soluble cell extracts and partially purified by DEAE-Sepharose chromatography. To measure NOS activity, 10 $\mu$L of enzyme is added to 40 $\mu$L of 50 mM Tris (pH 7.6) in the presence or absence of test compounds and the reaction initiated by the addition of 50 $\mu$L of a reaction mixture containing 50 mM Tris (pH 7.6), 2.0 mg/mL bovine serum albumin, 2.0 mM DTT, 4.0 mM CaCl$_2$, 20 $\mu$M FAD, 100 $\mu$M tetrahydrobiopterin, 0.4 mM NADPH and 60 $\mu$M L-arginine containing 0.9 $\mu$Ci of L-[2,3-$^3$H]-arginine. The final concentration of L-arginine in the assay is 30 $\mu$M. For hecNOS or hncNOS, calmodulin is included at a final concentration of 40–100 nM. Following incubation at 37° C. for 15 minutes, the reaction is terminated by addition of 400 $\mu$L of a suspension (1 part resin, 3 parts buffer) of Dowex 50W X-8 cation exchange resin in a stop buffer containing 10 mM EGTA, 100 mM HEPES, pH 5.5 and 1 mM L-citrulline. After mixing the resin is allowed to settle and L-[2,3-$^3$H]-Citrulline formation is determined by counting aliquots of the supernatant with a liquid scintillation counter. Results are reported in Table I as the IC$_{50}$ values of compounds for hiNOS, hecNOS and hncNOS.

Human Cartilage Explant Assay

Bone pieces are rinsed twice with Dulbecco's Phosphate Buffered Saline (GibcoBRL) and once with Dulbecco's Modified Eagles Medium (GibcoBRL) and placed into a petri dish with phenol red free Minimum Essential Medium (MEM) (GibcoBRL). Cartilage was cut into small explants of approximately 15–45 mg in weight and one or two explants per well are placed into either 96 or 48 well culture plates with 200–500 $\mu$L of culture media per well. The culture media was either a custom modification of Minimum Essential Medium(Eagle) with Earle's salts (GibcoBRL) prepared without L-Arginine, without L-Glutamine and without phenol red or a custom modification of serumless Neuman and Tytell (GibcoBRL) medium prepared without L-arginine, without insulin, without ascorbic acid, without L-glutamine and without phenol red. Both are supplemented before use with 100 $\mu$M L-Arginine (Sigma), 2 mM L-glutamine, 1×HL-1 supplement (BioWhittaker), 50 mg/ml ascorbic acid (Sigma) and 150 pg/ml recombinant human IL-1$\beta$ (RD Systems) to induce nitric oxide synthase. Compounds are then added in 10 $\mu$L aliquots and the explants incubated at 37° C. with 5% CO$_2$ for 18–24 hours. The day old supernatant is then discarded and replaced with fresh culture media containing recombinant human IL-1$\beta$ and compound and incubated for another 20–24 hours. This supernatant is analyzed for nitrite with a fluorometric assay (Misko et al, *Anal. Biochem.*, 214, 11–16, 1993). All samples are done in quadruplicate. Unstimulated controls are cultured in media in the absence of recombinant human IL-1$\beta$. IC$_{50}$ values (Table I) are determined from plotting the percent inhibition of nitrite production at six different concentrations of inhibitor.

TABLE I

| Example Number | IC$_{50}$ [$\mu$M] | | | |
| --- | --- | --- | --- | --- |
| | hiNOS | hecNOS | hncNOS | Human cartilage |
| 2 | 172 | 1490 | 523 | — |
| 6 | 0.9 | 89 | 8 | 0.1 |
| 8 | 20 | 418 | 150 | — |

In Vivo Assay

Rats can be treated with an intraperitoneal injection of 1–12.5 mg/kg of endotoxin (LPS) with or without oral administration of the nitric oxide synthase inhibitors. Plasma nitrite/nitrate levels can be determined 5 hours post-treatment. The results can be used to show that the administration of the nitric oxide synthase inhibitors decreases the rise in plasma nitrite/nitrate levels, a reliable indicator of the production of nitric oxide induced by endotoxin. As shown in Table II, Example 1 ((2S,5E)-2-amino-6-fluoro-7-[(1-iminoethyl)amino]-5-heptenoic acid, dihydrochloride) inhibited the LPS-induced increase in plasma nitrite/nitrate levels with an observed $ED_{50}$ value of <0.1 mg/kg, demonstrating the ability to inhibit inducible nitric oxide synthase activity in vivo.

What is claimed:

1. A compound of Formula I

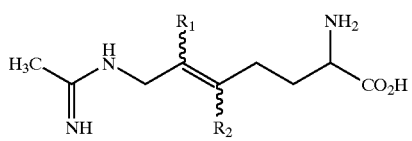

I or a pharmaceutically acceptable salt thereof, wherein:
$R_1$ is selected from the group consisting of H and methyl; and
$R_2$ is selected from the group consisting of H and methyl.

2. The compound as recited in claim 1 wherein:
$R_1$ is H; and
$R_2$ is selected from the group consisting of H and methyl.

3. The compound as recited in claim 1 wherein:
$R_1$ is H; and
$R_2$ is H.

4. The compound as recited in claim 1 wherein:
$R_1$ is H; and
$R_2$ is methyl.

5. The compound as recited in claim 1 wherein:
$R_1$ is methyl; and
$R_2$ is selected from the group consisting of H and methyl.

6. The compound as recited in claim 1 wherein:
$R_1$ is methyl; and
$R_2$ is H.

7. The compound as recited in claim 1 wherein:
$R_1$ is methyl; and
$R_2$ is methyl.

8. The compound as recited in claim 1 corresponding to Formula II

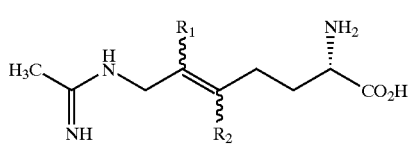

II or a pharmaceutically acceptable salt thereof, wherein:
$R_1$ is selected from the group consisting of H and methyl; and
$R_2$ is selected from the group consisting of H and methyl.

9. The compound as recited in claim 8 wherein:
$R_1$ is H; and
$R_2$ is selected from the group consisting of H and methyl.

10. The compound as recited in claim 9 wherein:
$R_1$ R is H; and
$R_2$ is H.

11. The compound as recited in claim 9 wherein:
$R_1$ is H; and
$R_2$ is methyl.

12. The compound as recited in claim 9 wherein:
$R_1$ is methyl; and
$R_2$ is selected from the group consisting of H and methyl.

13. The compound as recited in claim 9 wherein:
$R_1$ is methyl; and
$R_2$ is H.

14. The compound as recited in claim 9 wherein:
$R_1$ is methyl; and
$R_2$ is methyl.

15. The compound as recited in claim 1 corresponding to Formula III;

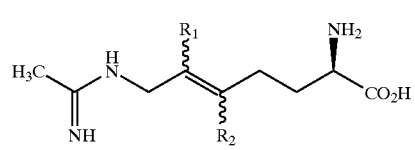

III or a pharmaceutically acceptable salt thereof, wherein:
$R_1$ is selected from the group consisting of H and methyl; and
$R_2$ is selected from the group consisting of H and methyl.

16. The compound as recited in claim 15 wherein:
$R_1$ is H; and
$R_2$ is selected from the group consisting of H and methyl.

17. The compound as recited in claim 15 wherein:
$R_1$ is H; and
$R_2$ is H.

18. The compound as recited in claim 15 wherein:
$R_1$ is H; and
$R_2$ is methyl.

19. The compound as recited in claim 15 wherein:
$R_1$ is methyl; and
$R_2$ is selected from the group consisting of H and methyl.

20. The compound as recited in claim 15 wherein:
$R_1$ is methyl; and
$R_2$ is H.

21. The compound as recited in claim 15 wherein:
$R_1$ is methyl; and
$R_2$ is methyl.

22. A compound as recited in claim 1 wherein the compound is the S enantiomer.

23. A compound as recited in claim 1 wherein the compound is the R enantiomer.

24. A compound as recited in claim 1 wherein the compound is the E isomer.

25. A compound as recited in claim 1 wherein the compound is the Z isomer.

26. A compound selected from the group consisting of:
(2S,5Z)-2-amino-6-methyl-7-[(1-iminoethyl)amino]-5-heptenoic acid, dihydrochloride, monohydrate;
(2S,5E)-2-amino-6-methyl-7-[(1-iminoethyl)amino]-5-heptenoic acid, dihydrochloride;
(2S,5Z)-2-amino-5,6-dimethyl-7-[(1-iminoethyl)amino]-5-heptenoic acid, dihydrochloride;
(2S,5Z)-2-amino-5-methyl-7-[(1-iminoethyl)amino]-5-heptenoic acid, dihydrochloride;
(2S,5E)-2-amino-5,6-dimethyl7-[(1-iminoethyl)amino]-5-heptenoic acid, dihydrochioride;

(2S,5Z)-2-amino-7-[(1-iminoethyl)amino]-5-heptenoic acid, dihydrochloride;

(2S,5E)-2-amino-5-methyl-7-[(1-iminoethyl)amino]-5-heptenoic acid, dihydrochloride;

(2S,5E)-2-amino-7-[(1-iminoethyl)amino]-5-heptenoic acid, dihydrochioride;

(2R,5Z)-2-amino-7-[(1-iminoethyl)amino]-5-heptenoic acid, dihydrochloride; and (2R,5E)-2-amino-7-[(1-iminoethyl)amino]-5-heptenoic acid, dihydrochloride.

27. A pharmaceutical composition comprising a compound of claim 1.

28. A method of lowering nitric oxide levels in a subject in need of such by administering a therapeutically effective amount of a compound of claim 26.

29. A method of inhibiting nitric oxide synthesis in a subject in need of such inhibition by administering a therapeutically effective amount of a compound of claim 26.

30. The method as recited in claim 29 wherein said nitric oxide synthase is an inducible nitric oxide synthase isoform, said inhibition selective for inducible nitric oxide synthase over the constitutive forms of nitric oxide synthase in a subject in need of such inhibition.

* * * * *